United States Patent
Spoors et al.

(10) Patent No.: US 8,242,290 B2
(45) Date of Patent: Aug. 14, 2012

(54) PROCESS FOR THE PREPARATION OF RENIN INHIBITORS

(75) Inventors: Paul G. Spoors, King of Prussia, PA (US); Lara S. Kallander, King of Prussia, PA (US); David A. Claremon, Maple Glen, PA (US)

(73) Assignee: Vitae Pharmaceuticals, Inc., Fort Washington, PA (US)

( * ) Notice: Subject to any disclaimer, the term of this patent is extended or adjusted under 35 U.S.C. 154(b) by 128 days.

(21) Appl. No.: 12/678,003

(22) PCT Filed: Sep. 17, 2008

(86) PCT No.: PCT/US2008/010814
§ 371 (c)(1),
(2), (4) Date: Jun. 23, 2010

(87) PCT Pub. No.: WO2009/038719
PCT Pub. Date: Mar. 26, 2009

(65) Prior Publication Data
US 2010/0256400 A1    Oct. 7, 2010

Related U.S. Application Data

(60) Provisional application No. 60/972,988, filed on Sep. 17, 2007, provisional application No. 61/087,431, filed on Aug. 8, 2008.

(51) Int. Cl.
*C07D 309/04* (2006.01)
*C07D 309/06* (2006.01)
(52) U.S. Cl. ............................................... 549/426
(58) Field of Classification Search .................... 549/426
See application file for complete search history.

(56) References Cited

FOREIGN PATENT DOCUMENTS
WO    WO 2007/070201 A1    6/2007
WO    WO 2009/038715 A1    3/2009

OTHER PUBLICATIONS

Notification Concerning Transmittal of the International Search Report and the Written Opinion of the International Searching Authority, International Application No. PCT/US2008/010814, mail date Dec. 18, 2008.
Notification Concerning Transmittal of International Preliminary Report on Patentability, and International Preliminary Report on Patentability, International Application No. PCT/US2008/010814, mail date Apr. 1, 2010.
Notification Concerning Transmittal of the International Search Report and the Written Opinion of the International Searching Authority, International Application No. PCT/US2008/010810, mail date Jan. 21, 2009.
Notification Concerning Transmittal of International Preliminary Report on Patentability, and International Preliminary Report on Patentability, International Application No. PCT/US2008/010810, mail date Apr. 1, 2010.
Office Communication, U.S. Appl. No. 12/678,007; 371(c) Filing Date: Jul. 12, 2010; Date of Communication: Apr. 20, 2012.

*Primary Examiner* — Bernard Dentz
(74) *Attorney, Agent, or Firm* — Hamilton, Brook, Smith & Reynolds, P.C.

(57) ABSTRACT

Disclosed is a process for the preparation of a tetrahydropyran-di-amine represented by Structural Formula (I): wherein $R_1$ is H or alkyl and E is H or an amine protecting group.

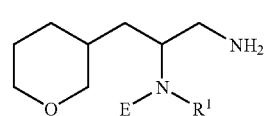

(I)

9 Claims, No Drawings

PROCESS FOR THE PREPARATION OF RENIN INHIBITORS

RELATED APPLICATIONS

This application is the U.S. National Stage of International Application No. PCT/US2008/010814, filed Sep. 17, 2008, which designates the U.S., published in English, and claims the benefit of U.S. Provisional Application No. 60/972,988, filed on Sep. 17, 2007, and U.S. Provisional Application No. 61/087,431 filed on Aug. 8, 2008. The entire teachings of the above applications are incorporated herein by reference.

BACKGROUND OF THE INVENTION

Aspartic proteases, including renin, β-secretase (BACE), HIV protease, HTLV protease and plasmepsins I and II, are implicated in a number of disease states. In hypertension, elevated levels of angiotensin I, the product of renin catalyzed cleavage of angiotensinogen are present. Elevated levels of β amyloid, the product of BACE activity on amyloid precursor protein, are widely believed to be responsible for the amyloid plaques present in the brains of Alzheimer's disease patients. The viruses HIV and HTLV depend on their respective aspartic proteases for viral maturation. *Plasmodium falciparum* uses plasmepsins I and II to degrade hemoglobin.

In the renin-angiotensin-aldosterone system (RAAS), the biologically active peptide angiotensin II (Ang II) is generated by a two-step mechanism. The highly specific aspartic protease renin cleaves angiotensinogen to angiotensin I (Ang I), which is then further processed to Ang II by the less specific angiotensin-converting enzyme (ACE). Ang II is known to work on at least two receptor subtypes called $AT_1$ and $AT_2$. Whereas $AT_1$ seems to transmit most of the known functions of Ang II, the role of $AT_2$ is still unknown.

Modulation of the RAAS represents a major advance in the treatment of cardiovascular diseases (Zaman, M. A. et al *Nature Reviews Drug Discovery* 2002, 1, 621-636). ACE inhibitors and $AT_1$ blockers have been accepted as treatments of hypertension (Waeber B. et al., "The renin-angiotensin system: role in experimental and human hypertension," in Berkenhager W. H., Reid J. L. (eds): *Hypertension*, Amsterdam, Elsevier Science Publishing Co, 1996, 489-519; Weber M. A., *Am. J. Hypertens.*, 1992, 5, 247S). Interest in the development of renin inhibitors stems from the specificity of renin (Kleinert H. D., *Cardiovasc. Drugs*, 1995, 9, 645). The only substrate known for renin is angiotensinogen, which can only be processed (under physiological conditions) by renin. Renin inhibitors are not only expected to be superior to ACE inhibitors and $AT_1$ blockers with regard to safety, but more importantly also with regard to their efficacy in blocking the RAAS.

Recently, non-peptide renin inhibitors were described which show high in vitro activity (Oefner C. et al., Chem. Biol., 1999, 6, 127; Maerki H. P. et al., Il Farmaco, 2001, 56, 21 and International Patent Application Publication No. WO 97/09311). Other non-peptide renin inhibitors have been described in International Patent Application Nos. PCT/US2005/03620 (WO2006/042150), PCT/US2007/008520, and PCT/US2006/043920 (WO2007/070201) and U.S. Provisional Patent Application Nos. 60/845,331 and 60/845,291), the disclosures of each of which are incorporated herein by reference. An example of such aspartic protease/renin inhibitors is a compound represented by Formula (A):

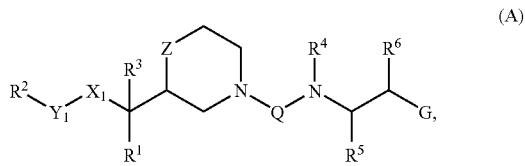

wherein the substituents: $R^1$, $R^2$, $R^3$, $R^4$, $R^5$, $R^6$, $X_1$, $Y_1$, Z, Q and G are as defined in PCT/US2006/043920 (WO2007/070201). Another example of an aspartic protease/renin inhibitor is a compound represented by Formula (A-1):

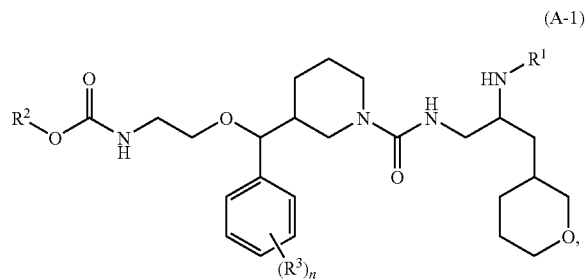

and more specifically a compound represented by Formula (A-2):

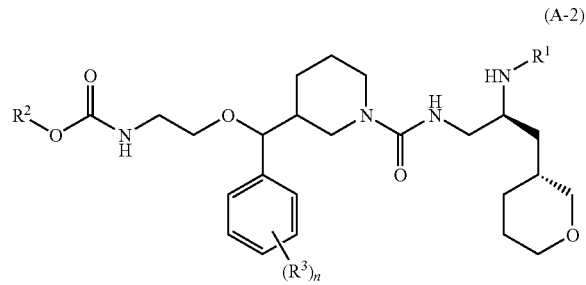

or a pharmaceutically acceptable salt thereof, wherein: $R^1$ is H or alkyl; $R^2$ is alkyl, cycloalkyl or cycloalkylalkyl; $R^3$ is F, Cl, Br, cyano, nitro, alkyl, haloalkyl, alkoxy, haloalkoxy, or alkanesulfonyl; and n is 0, 1, 2, or 3.

The process of forming an aspartic acid protease inhibitor, e.g., represented by Formula (A-1) or (A-2), above, is exemplified in the following scheme:

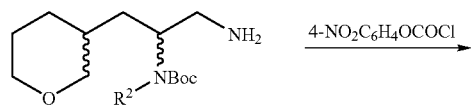

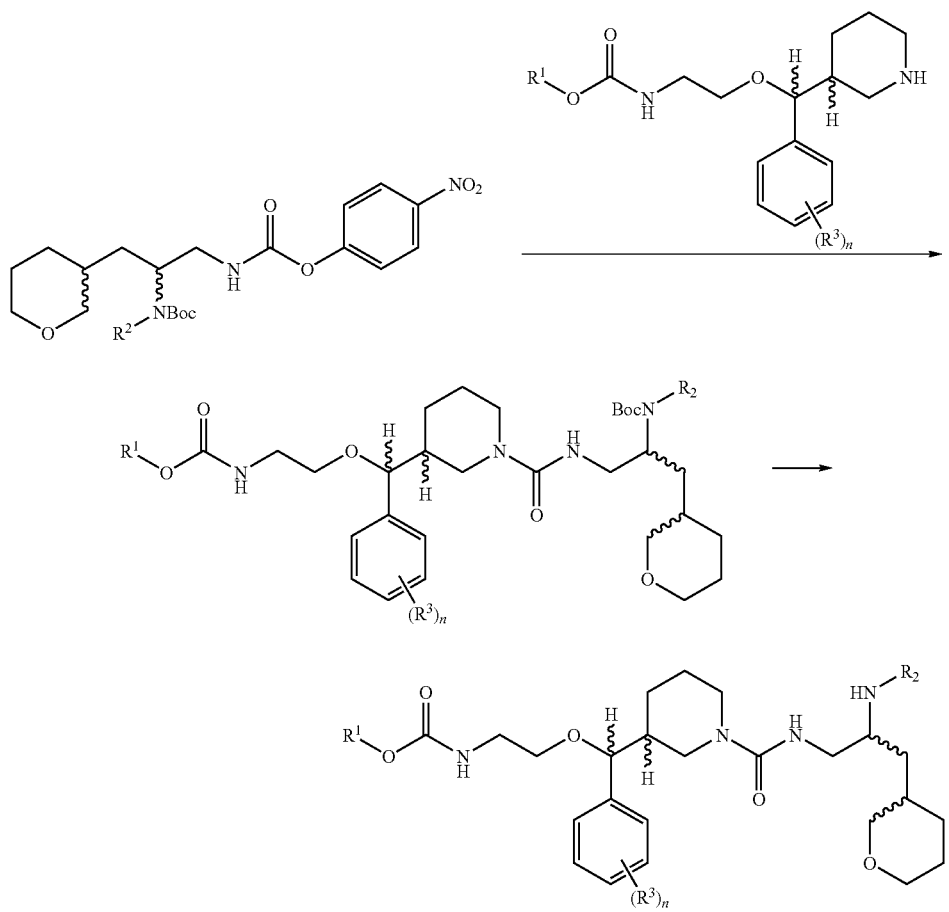

Specific conditions for carrying out the above reactions are provided in PCT/US2006/043920 (WO2007/070201), the entire teachings of which are incorporated herein by reference.

Significant quantities of the pure aspartic protease/renin inhibitor are required in the drug development process, e.g., for in vitro and in vivo testing, as formulated and/or unformulated drug substance. Accordingly, it would be useful to develop efficient processes for the large-scale preparation of such aspartic protease/renin inhibitor compounds and the intermediates used therein.

SUMMARY OF THE INVENTION

This invention is directed to a process for the preparation of a tetrahydropyran-di-amine represented by Structural Formula (I):

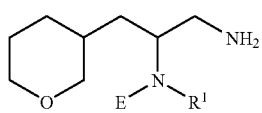
(I)

wherein $R^1$ is H or $(C_1-C_6)$alkyl and E is H or an amine protecting group, wherein the process comprises the steps of:

1) hydrogenating a dihydropyran-ene-amine having the formula:

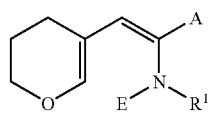

wherein A is a carbonyl-containing moiety, to form a dihydropyran-amine having the formula:

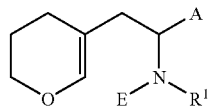

2) hydrogenating the dihydropyran-amine to form a tetrahydropyran-amine having the formula:

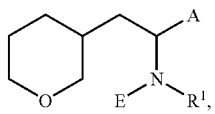, and 3) converting the tetrahydropyran-amine into the tetrahydropyran-di-amine.

Another embodiment of the invention are the intermediates and products disclosed herein.

DETAILED DESCRIPTION OF THE INVENTION

In another embodiment, this invention is directed to a process for the preparation of a tetrahydropyran-di-amine represented by Structural Formulas (Ia), (Ib), (Ic), and (Id):

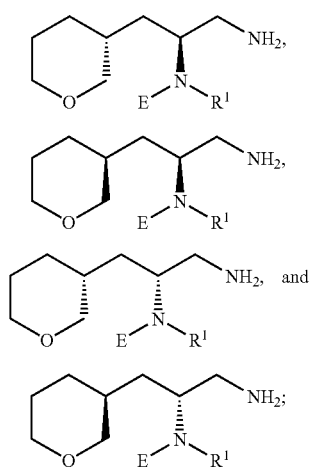

wherein $R^1$ is H or $(C_1$-$C_6)$alkyl and E is H or an amine protecting group.

"Alkyl" means a saturated aliphatic branched or straight-chain hydrocarbon radical. Alkyls commonly have from one to six carbon atoms, typically from one to three carbon atoms. Thus, "$(C_1$-$C_3)$alkyl" means a radical having from 1-3 carbon atoms in a linear or branched arrangement. "$(C_1$-$C_3)$alkyl" includes methyl, ethyl, propyl and isopropyl.

In the processes of this invention, when E is an amine protecting group, it is understood the E many be any amine protecting group that is compatible with the processes of this invention. Such amine protecting groups are well-known in the art (See T. W. Greene and P. G. M. Wuts "Protective Groups in Organic Synthesis" John Wiley & Sons, Inc., New York 1999). For example, E may be selected from a carbamate, amide, formate, or sulfonamide protecting group. Exemplary amine protecting groups include tert-butoxycarbonyl (Boc), benzyloxycarbonyl (Cbz) and 1-[2-(trimethylsily)ethoxycarbonyl] (Teoc).

In the process of this invention, substituent "A" is a carbonyl-containing moiety, such as a carboxylic acid (—$CO_2H$), an ester (—$CO_2R'$), an anhydride (—CO—O—COR') or an amide (—$CONH_2$ or —CONHR') moiety (wherein R' is $(C_1$-$C_4)$alkyl, phenyl, benzyl, p-methoxybenzyl, etc.) that can be converted to a methylene-amine (—$CH_2NH_2$) moiety via conventional transformations. For example, A may be an amide moiety that can be reduced using conventional reducing agents to form a methylene amino group (e.g., R—$CO_2NH_2$→R—$CH_2NH_2$). In a specific embodiment of this invention, A is a carboxylic acid moiety that may be converted to a methylene amino group, for example by first converting the carboxylic acid moiety into an amide moiety by routine coupling reactions, which may then be reduced using conventional reducing agents to form the methylene amino group (e.g., R—$CO_2H$→R—$CO_2NH_2$→R—$CH_2NH_2$).

Although it is anticipated that dihydropyran-ene amine compounds (e.g., as used in step 1) containing various combinations of E (amine protecting) groups and A (carbonyl-containing) groups will be useful in the method of this invention, it was observed that the dihydropyran-ene-amine compound having E=CBz and A=$CO_2CH_3$ was a relatively unstable compound. Dihydropyran-ene amine compounds where A=a carboxylic acid group appear to be more stable and therefore, more suitable to scale-up. In the specific examples provided herein E=Boc and A=$CO_2H$.

The tetrahydropyran amines, tetrahydropyran di-amines, dihydropyran amines, and dihydropyran ene-amines may exist in various stereoisomeric forms, e.g., as exemplified above in formulas (Ia)-(Id). Stereoisomers are compounds which differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that contain two or more asymmetrically substituted carbon atoms. "R" and "S" represent the configuration of substituents around each one or more chiral carbon atoms. When a chiral center is not defined as R or S and the configuration at the chiral center is not defined by other means, either configuration can be present or a mixture of both configurations can be present.

"Racemate" or "racemic mixture" means a compound of equimolar quantities of two enantiomers, wherein such mixtures exhibit no optical activity; i.e., they do not rotate the plane of polarized light.

"R" and "S" indicate configurations relative to the core molecule.

"⁓" and "⁓" represent "⦀", "◼" or "___", wherein when "⁓" or "⁓" is used to depict an enantiomer (e.g., "⦀" or "◼"), that enantiomer is at least 60%, 70%, 80%, 90%, 99% or 99.9% optically pure.

The processes disclosed herein provide tetrahydropyran amines, tetrahydropyran di-amines, or dihydropyran amines as racemic mixtures or as enantiomerically or diastereomerically enriched mixtures. Such enantiomerically or diastereomerically enriched mixtures are at least 60%, 70%, 80%, 90%, 99% or 99.9% optically pure. Purified, individual isomers (enantiomers or diastereomers) may be obtained by resolution from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture using various well known chromatographic methods.

When the stereochemistry of the tetrahydropyran amines, tetrahydropyran di-amines, or dihydropyran amines are named or depicted by structure, the named or depicted stereoisomer(s) is (are) at least 60%, 70%, 80%, 90%, 99% or 99.9% by weight pure relative to the other stereoisomers. When a single enantiomer is named or depicted by structure, the depicted or named enantiomer is at least 60%, 70%, 80%, 90%, 99% or 99.9% optically pure.

Salts, specifically pharmaceutically acceptable salts, of the disclosed tetrahydropyran amines, tetrahydropyran di-amines, dihydropyran amines or dihydropyran ene-amines may be obtained by reacting the amine compound with a suitable organic or inorganic acid, resulting in pharmaceutically acceptable anionic salt forms. Examples of anionic salts include the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylsulfate, mucate, napsylate, nitrate, pamoate, pantothenate, phosphate/diphospate, polygalacturonate, salicylate, stearate, subacetate, succinate, sulfate, tannate, tartrate, teoclate, tosylate, and triethiodide salts.

Salts of tetrahydropyran amines, dihydropyran amines or dihydropyran ene-amines that also contain a carboxylic acid or other acidic functional group may be prepared by reacting with a suitable base. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bisdehydroabietylamine, glucamine, N-methylglucamine, collidine, quinine, quinoline, and basic amino acids such as lysine and arginine.

It may be necessary and/or desirable during synthesis to protect sensitive or reactive groups on any of the molecules concerned. Representative conventional protecting groups are described in T. W. Greene and P. G. M. Wuts "Protective Groups in Organic Synthesis" John Wiley & Sons, Inc., New York 1999, and the entire teaching of which is herein incorporated by reference. Protecting groups may be added and removed using methods well known in the art.

Because the process of this invention forms 2 separate chiral centers in two separate hydrogenation steps, the opportunity exists to form either racemic compounds, by using conventional hydrogenation catalysts (e.g., [Rh(COD)$_2$] BF$_4$), or to form chiral compounds by using chiral hydrogenation catalysts for either one or both of the hydrogenation steps. The use of chiral hydrogenation catalysts for both hydrogenations provides compounds that are diastereomerically enriched.

For example, the use of a chiral hydrogenation catalyst in the first hydrogenation step, that is, the conversion of the dihydropyran ene-amine to the dihydropyran amine, would provide an enantiomerically enriched tetrahydropyran-di-amine having the formula:

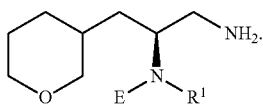

wherein $R^1$ is H or $(C_1\text{-}C_6)$alkyl and E is H or an amine protecting group. This enantiomerically enriched tetrahydropyran-di-amine is prepared by the process comprising the steps of:

1) hydrogenating a dihydropyran-ene-amine having the formula:

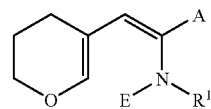

wherein A is a carbonyl-containing moiety, to form a dihydropyran-amine having the formula:

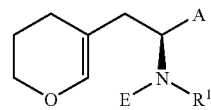

2) hydrogenating the dihydropyran-amine to form a tetrahydropyran-amine having the formula:

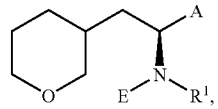

and 3) converting the tetrahydropyran-amine into the tetrahydropyran-di-amine.

Another embodiment of the invention is the reaction of the step 1) above. Another embodiment of the invention is the reaction of the step 2) above. Another embodiment of the invention is the reaction of the step 3) above.

The use of chiral hydrogenation catalysts in each hydrogenation step would provide a diastereomerically enriched tetrahydropyran-di-amine having the formula:

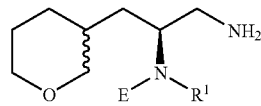

wherein the process comprises the steps of:

1) hydrogenating a dihydropyran-ene-amine having the formula:

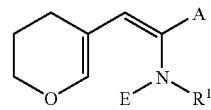

to form a dihydropyran-amine having the formula:

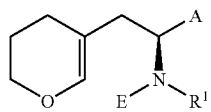

2) hydrogenating the dihydropyran-amine to form a tetrahydropyran-amine having the formula:

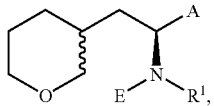

and 3) converting the tetrahydropyran-amine into the tetrahydropyran-di-amine.

Another embodiment of the invention is the reaction of the step 1) above. Another embodiment of the invention is the reaction of the step 2) above. Another embodiment of the invention is the reaction of the step 3) above.

In specific embodiments of this invention, $R^1$ is methyl, E is a carbamate group, specifically a tert-butoxycarbonyl group, and A is an acid moiety (—$CO_2H$). In a more specific embodiment, this invention is directed to a process for the preparation of a tetrahydropyran-di-amine having the formula:

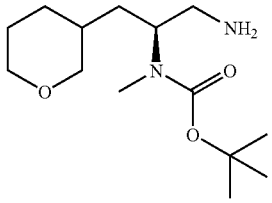

wherein the process comprises the steps of:

1) hydrogenating a dihydropyran-ene-amine having the formula:

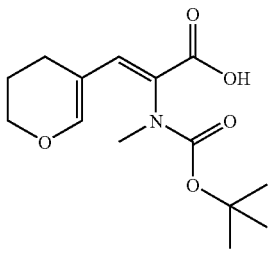

to form a dihydropyran-amine having the formula:

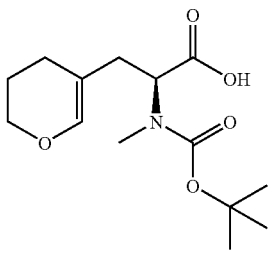

2) hydrogenating the dihydropyran-amine to form a tetrahydropyran-amine acid having the formula:

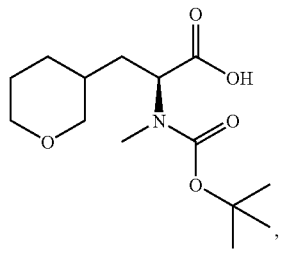

and 3) converting the tetrahydropyran-amine acid into the tetrahydropyran-di-amine.

Another embodiment of the invention is the reaction of the step 1) above. Another embodiment of the invention is the reaction of the step 2) above. Another embodiment of the invention is the reaction of the step 3) above.

In another specific embodiment, this invention is directed to a process for the preparation of a tetrahydropyran amine acid having the formula:

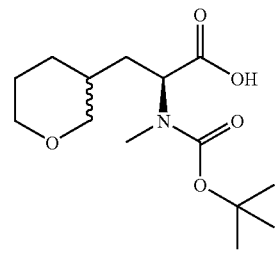

wherein the process comprises the steps of:

1) hydrogenating a dihydropyran-ene-amine having the formula:

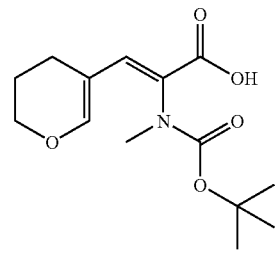

to form a dihydropyran-amine having the formula:

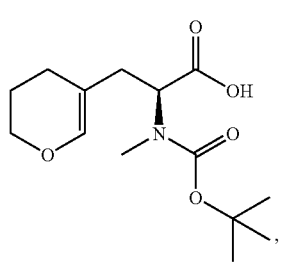

and 2) hydrogenating the dihydropyran-amine to form the tetrahydropyran-amine acid.

Another embodiment of the invention is the reaction of the step 1) above. Another embodiment of the invention is the reaction of the step 2) above.

The chiral catalyst used in the hydrogenation of t-Boc protected dihydropyran ene-amine can be, for example, a catalyst generated from [Rh(nbd)$_2$]BF$_4$ and SL-M004-1 (catalyst loading is, for example, 1-2 mol %; SL-M004-1: (αR,αR)-2,2'-bis(α-N,N-dimethyl-aminophenylmethyl)-(S,S)-1,1'-bis[di(3,5-dimethyl-4-methoxyphenyl)phosphino]ferrocene). In one exemplification of the process of this invention, the t-Boc protected dihydropyran ene-amine was hydrogenated in methanol, at 25° C., using about 88-110 psi hydrogen pressure, using a catalyst generated from [Rh(nbd)$_2$]BF$_4$ and SL-M004-1 (catalyst loading 1-2 mol %; SL-M004-1: (αR,αR)-2,2'-bis(α-N,N-dimethyl-aminophenylmethyl)-(S,S)-1,1'-bis[di(3,5-dimethyl-4-methoxyphenyl)phosphino]ferrocene) to provide the t-Boc protected dihydropyran amine in >90% ee. The catalyst used in the second hydrogenation may be a conventional catalyst or another chiral catalyst. Use of a conventional catalyst provides a tetrahydropyran-amine acid (and subsequently the tetrahydropyran di-amine) having only one chiral center enantiomerically enriched by this synthetic route. The use of a second chiral hydrogenation catalyst provides diastereomerically enriched tetrahydropyran amine acid.

The chiral catalyst for the hydrogenation of the dihydropyran-ene-amine can be, for example, Rh(COD)$_2$O$_3$SCF$_3$ and SL-A109-2 (the solvent, for example, is tetrahydrofuran) or [Rh(nbd)$_2$]BF$_4$ and SL-A109-2 (the solvent is, for example: methanol) (SL-A 109-2: (S)-(6,6'-dimethoxybiphenyl-2,2'-diyl)-bis[bis(3,5-di-tert-butyl-4-methoxyphenyl)phosphine]. For example, hydrogenation of the dihydropyran-ene-amine at 50° C., using about 80 bar hydrogen pressure and 4 mol % catalyst loading of Rh(COD)$_2$O$_3$SCF$_3$ and SL-A109-2 (solvent: THF) or [Rh(nbd)$_2$]BF$_4$ and SL-A109-2 (solvent: methanol) (SL-A109-2: (S)-(6,6'-dimethoxybiphenyl-2,2'-diyl)-bis[bis(3,5-di-tert-butyl-4-methoxyphenyl)phosphine] provides the tetrahydropyran amine acid having a diastereomeric ratio (dr) of >80:20.

Preferably, the hydrogenation of the dihydropyran amine is conducted using SL-F365-1 as the chiral ligand (SL-F365-1: 1-[(S)-ferrocenyl-2-(R)-ethyl-1-dimethylamino)cyclohexyl]-(S)-phosphino-1'-dicyclohexylphosphino-ferrocene; CAS Registry Number: 952687-84-2; available from Solvias, Inc. Fort Lee, N.J.). Hydrogenation of the dihydropyran amine at 70° C., using about 50 bar hydrogen pressure and 0.4 mol % catalyst loading of [Rh(nbd)$_2$]BF$_4$ and SL-F365-1 (solvent: n-butanol) provides the tetrahydropyran amine acid having a diastereomeric ratio (dr) of about 95:5 and at about 95% conversion.

Alternatively, the hydrogenation may be conducted using SL-A240-1 as the chiral ligand (SL-A240-1: (R)-(+)-5,5'-bis[di(3,5-xylyl)phosphino]-4,4'-bi-1,3-benzodioxole [(4R)-(4,4'-bi-1,3-benzodioxole)-5,5'-diyl]bis[bis(3,5-dimethylphenyl)phosphine] also known as (R)-DM-SEGPHOS®). Hydrogenation of the dihydropyran amine at 40° C., using about 50 bar hydrogen pressure and 0.4 mol % catalyst loading of Rh(COD)$_2$O$_3$SCF$_3$ and SL-A240-1 (solvent: THF) provides the tetrahydropyran amine acid having a diastereomeric ratio (dr) of about 5:95 and at about 79% conversion.

The process of this invention further comprises the steps of:

1) converting a tetrahydropyran-amine acid into a tetrahydropyran amine amide having the formula:

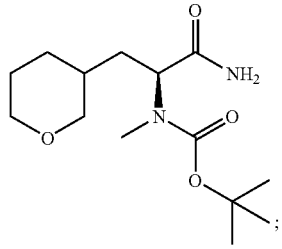

and 2) converting the tetrahydropyran-amine amide into the tetrahydropyran di-amine having the formula:

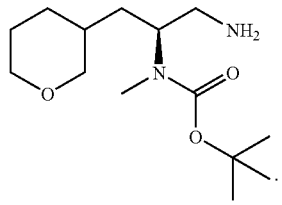

The tetrahydropyran-amine acid can be converted into a tetrahydropyran-amine amide by first converting the carboxylic acid group into an "activated ester" intermediate and then reacting the activated ester intermediate with ammonia. An ester —COOR is said to be "activated" when —OR is readily displaced by an amine. —OR is more easily displaced as R becomes more electron withdrawing.

Formation of an activated ester typically requires a "coupling agent", also referred to as a "carboxylic acid activating agent", which is a reagent that replaces the hydroxyl group of a carboxyl acid with a group which is susceptible to nucleophilic displacement. Examples of coupling agents include 1,1'-carbonyldiimidazole (CDI), isobutyl chloroformate, dimethylaminopropylethyl-carbodiimide (EDC), dicyclohexyl carbodiimide (DCC). Standard conditions can be used to carry out this reaction. Exemplary conditions are provided in Example 5.

The tetrahydropyran-amine amide can be converted into a tetrahydropyrandiamine with an amide reducing agent. An "amide reducing agent" is a reagent which can reduce an amide to an amine. Such reagents are known in the art and are disclosed in, for example, in March, "Advanced Organic Chemistry—Reactions, Mechanisms and Structure", Third Edition, John Wiley & Sons, 1985, pages 1099-1100, Brown and Krishnamurthy, *Aldrichimica Acta* 12:3 (1979) and references cited therein. Examples include lithium aluminum hydride, lithium triethyl borohydride, borane reagents (e.g., boraneÿtetrahydrofuran, boraneÿmethyl sulfide, disiamylborane, and the like), aluminum hydride, lithium trimethoxy aluminum hydride and triethyloxonium fluoroborate/sodium borohydride. Standard conditions can be used to carry out this reaction. Exemplary conditions are provided in Example 5.

The invention is further defined by reference to the examples, which are intended to be illustrative and not limiting.

Representative compounds of the invention can be synthesized in accordance with the general synthetic schemes described above and are illustrated in the examples that follow. The methods for preparing the various starting materials used in the schemes and examples are well within the knowledge of persons skilled in the art.

The following abbreviations have the indicated meanings:

| Abbreviation | Meaning |
| --- | --- |
| Aq | Aqueous |
| Boc | tert-butoxy carbonyl or t-butoxy carbonyl |
| (Boc)$_2$O | di-tert-butyl dicarbonate |
| CDI | carbonyl diimidazole |
| DPPF | 1,1'-Bis(diphenylphosphino)ferrocene |
| Equiv | Equivalents |
| Et | Ethyl |
| Et$_3$N | Triethyl amine |
| h, hr | Hour |
| HCl | Hydrochloric acid |
| LHMDS | lithium hexamethyldisilazane |
| LiOH | lithium hydroxide |
| LAH or LiAlH$_4$ | lithium aluminum hydride |
| LC-MS | liquid chromatography-mass spectroscopy |
| LHMDS | lithium hexamethyldisilazane |
| Me | Methyl |
| MeOH | Methanol |
| Min | Minute |
| MS | mass spectrum |
| NaHCO$_3$ | sodium bicarbonate |
| NMM | N-methylmorpholine |
| NMP | N-methylpyrrolidinone |
| Pd$_2$(dba)$_3$ | Tris(dibenzylideneacetone)dipalladium(0) |
| Ph | Phenyl |
| rt | room temperature |
| TEA | triethylamine or Et$_3$N |
| Teoc | 1-[2-(trimethylsilyl)ethoxycarbonyloxy]- |
| Teoc-OSu | 1-[2-(trimethylsilyl)ethoxycarbonyloxy]pyrrolidin-2,5-dione |
| TFA | trifluoroacetic acid |
| THF | Tetrahydrofuran |

Example 1

(2Z)-3-(3,4-Dihydro-2H-pyran-5-yl)-2-[{[(1,1-dimethylethyl)oxy]carbonyl}(methyl)amino]-2-propenoic acid may be prepared as follows:

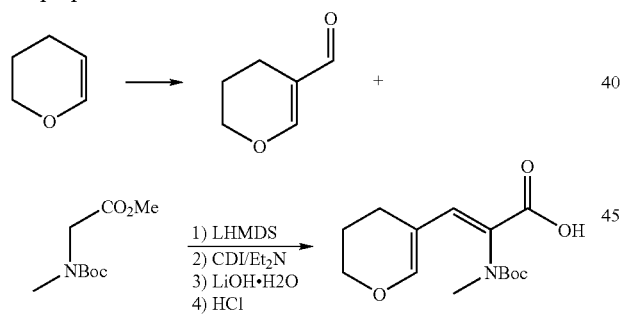

The propenoic acid was prepared as described above from the dihydropyran aldehyde. See also U.S. Pat. No. 2,517,543.

Example 2

3-(3,4-Dihydro-2H-pyran-5-yl)-N-{[(1,1-dimethylethyl)oxy]carbonyl}-N-methyl-L-alanine may be prepared as follows:

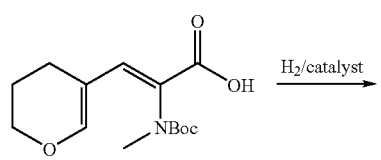

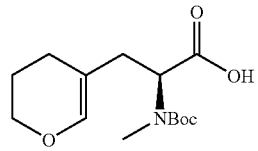

The t-Boc protected dihydropyran ene-amino acid was hydrogenated (6 bar-110 psi) at room temperature (approx. 25° C.) in methanol using a catalyst generated from [Rh(nbd)$_2$]BF$_4$ and SL-M004-1 (SL-M004-1: (αR,αR)-2,2'-bis(α-N,N-dimethyl-aminophenylmethyl)-(S,S)-1,1'-bis[di(3,5-dimethyl-4-methoxyphenyl)phosphino]ferrocene, available from Solvias, Inc. Fort Lee, N.J.). (>90% ee)

Example 3

N-{[(1,1-Dimethylethyl)oxy]carbonyl}-N-methyl-3-(tetrahydro-2H-pyran-3-yl)-L-alanine may be prepared as follows:

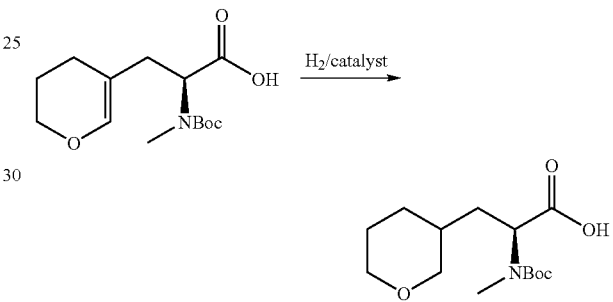

The tetrahydropyran amino acid was formed by hydrogenation of the dihydropyran amino acid using [Rh(COD)$_2$]BF$_4$ and DPPF at 70° C. for 2 days.

Example 4 tert-Butyl-1-amino-3-tetrahydro-2H-pyran-3-yl)propan-2-yl(methyl)carbamate may be prepared as follows:

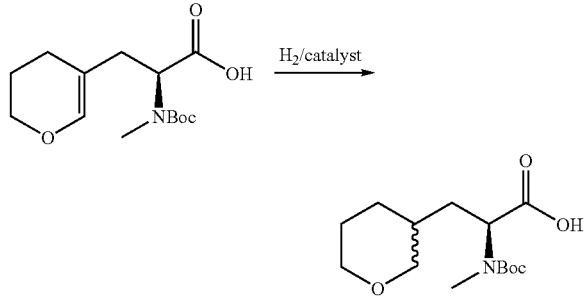

The diastereomerically enriched tetrahydropyran amino acid was formed by hydrogenation of the dihydropyran amino acid using 80 bar hydrogen pressure at 50° C. and 4 mol % of a catalyst generated from [Rh(COD)$_2$]O$_3$SCF$_3$ and SL-A109-2 (solvent: THF) or [Rh(nbd)$_2$]BF$_4$ and SL-A109-2 (solvent: methanol) (SL-A109-2: (S)-(6,6'-dimethoxybiphenyl-2,2'-diyl)-bis[bis(3,5-di-tert-butyl-4-methoxyphenyl)phosphine], available from Solvias, Inc. Fort Lee, N.J.). (>80:20 dr)

Example 5 tert-Butyl(S)-1-amino-3-(tetrahydro-2H-pyran-3-yl)propan-2-yl(methyl)carbamate may be prepared as follows:

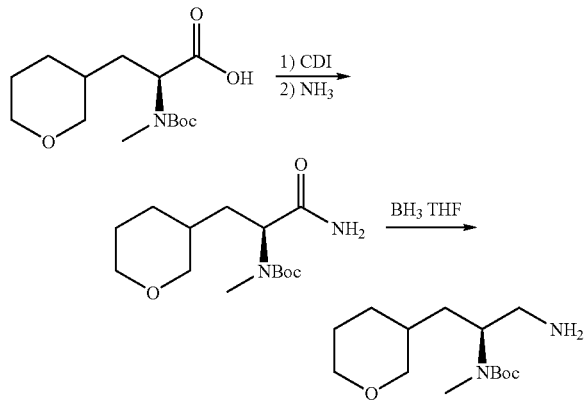

The tetrahydropyran amino acid was converted to the tetrahydropyran amino amide using CDI and aq. NH₃. Reduction of the tetrahydropyran amide using BH₃-THF provided the tetrahydropyran di-amine.

Example 6 tert-Butyl-1-amino-3-tetrahydro-2H-pyran-3-yl)propan-2-yl(methyl)carbamate may be prepared as follows:

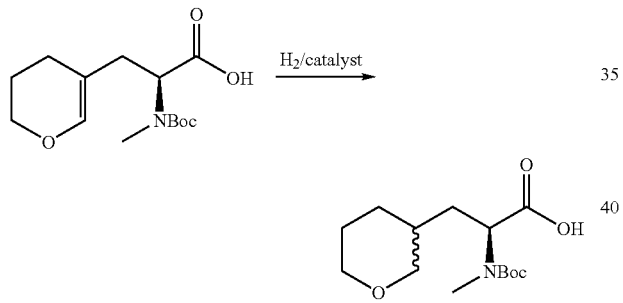

The diastereomerically enriched tetrahydropyran amino acid was formed by hydrogenation of the dihydropyran amino acid using 50 bar hydrogen pressure at 70° C. and 4 mol % of a catalyst generated from [Rh(nbd)₂]BF₄ and SL-F365-1 (solvent: n-butanol) (SL-F365-1: 1-[(S)-ferrocenyl-2-(R)-ethyl-1-dimethylamino)cyclohexyl]-(S)-phosphino-1'-dicyclohexylphosphino-ferrocene; CAS Registry Number: 952687-84-2; available from Solvias, Inc. Fort Lee, N.J.). The tetrahydropyranyl product was obtained in 95:5 dr and 95% conversion.

Example 7 tert-Butyl-1-amino-3-tetrahydro-2H-pyran-3-yl)propan-2-yl(methyl)carbamate may be prepared as follows:

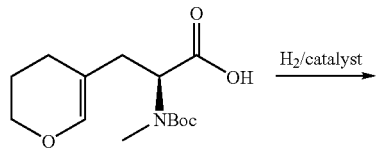

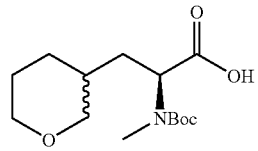

The diastereomerically enriched tetrahydropyran amino acid was formed by hydrogenation of the dihydropyran amino acid using 50 bar hydrogen pressure at 40° C. and 4 mol % of a catalyst generated from Rh(COD)₂]O₃SCF₃ and SL-A240-1 (solvent: THF) (SL-A240-1: (R)-(+)-5,5'-bis[di(3,5-xylyl)phosphino]4,4'-bi-1,3-benzodioxole[(4R)-(4,4'-bi-1,3-benzodioxole)-5,5'-diyl]bis[bis(3,5-dimethylphenyl)phosphine] also known as (R)-DM-SEGPHOS®). The tetrahydropyranyl product was obtained in 5:95 dr and 79% conversion.

While this invention has been particularly shown and described with references to specific embodiments thereof, it will be understood by those skilled in the art that various changes in form and details may be made therein without departing from the scope of the invention encompassed by the appended claims.

What is claimed is:

1. A process for the preparation of a tetrahydropyran-di-amine represented by Structural Formula (I):

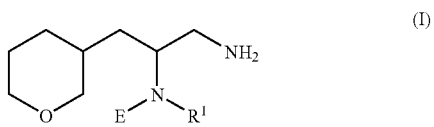

wherein R¹ is H or (C₁-C₆)alkyl and E is H or an amine protecting group, wherein the process comprises the steps of:

a) hydrogenating a dihydropyran-ene-amine having the formula:

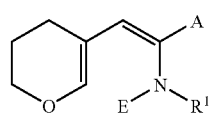

wherein A is a carbonyl-containing moiety, to form a dihydropyran-amine having the formula:

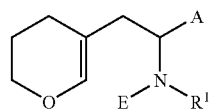

b) hydrogenating the dihydropyran-amine to form a tetrahydropyran-amine having the formula:

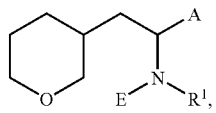

and c) converting the tetrahydropyran-amine into the tetrahydropyran-di-amine.

2. The process according to claim 1, wherein E is tert-butoxycarbonyl, benzyloxycarbonyl or 1-[2-(trimethylsilyl)ethoxycarbonyl].

3. The process according to claim 1, wherein E is tert-butoxycarbonyl.

4. The process according to claim 1, wherein substituent A is —CO₂H.

5. A process for the preparation of a tetrahydropyran-di-amine having the formula:

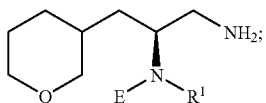

wherein R¹ is H or (C₁-C₆)alkyl and E is H or an amine protecting group, wherein the processes comprises the steps of:

a) hydrogenating a dihydropyran-ene-amine having the formula:

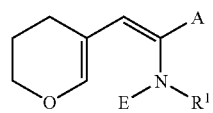

wherein A is a carbonyl-containing moiety, to form a dihydropyran-amine having the formula:

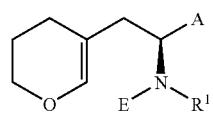

b) hydrogenating the dihydropyran-amine to form a tetrahydropyran-amine having the formula:

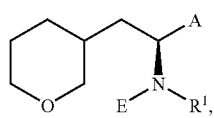

and c) converting the tetrahydropyran-amine into the tetrahydropyran-di-amine.

6. A process for the preparation of a tetrahydropyran-di-amine having the formula:

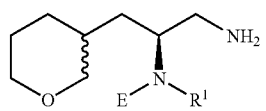

wherein the process comprises the steps of:

a) hydrogenating a dihydropyran-ene-amine having the formula:

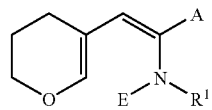

to form a dihydropyran-amine having the formula:

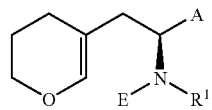

b) hydrogenating the dihydropyran-amine to form a tetrahydropyran-amine having the formula:

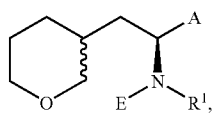

and c) converting the tetrahydropyran-amine into the tetrahydropyran-di-amine.

7. A process for the preparation of a tetrahydropyran-di-amine having the formula:

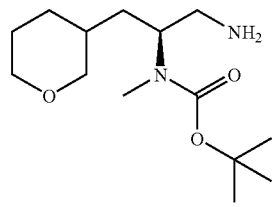

wherein the process, comprises the steps of:

a) hydrogenating a dihydropyran-ene-amine having the formula:

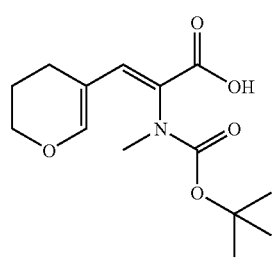

to form a dihydropyran-amine having the formula:

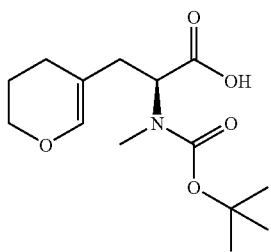

b) hydrogenating the dihydropyran-amine to form a tetrahydropyran-amine acid having the formula:

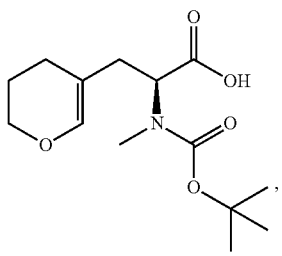

and c) converting the tetrahydropyran-amine acid into the tetrahydropyran-di-amine.

8. The process according to claim 7, further comprising the steps of:

a) converting the tetrahydropyran-amine acid into a tetrahydropyran amino amide having the formula:

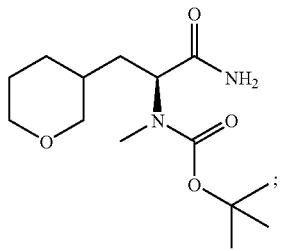

and b) converting the tetrahydropyran-amino amide into the tetrahydropyran di-amine.

9. A process for the preparation of a tetrahydropyran amine acid having the formula:

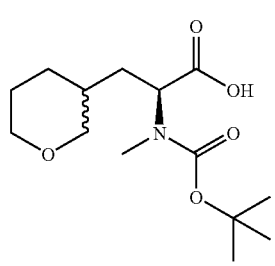

wherein the process comprises the steps of:

a) hydrogenating a dihydropyran-ene-amine having the formula:

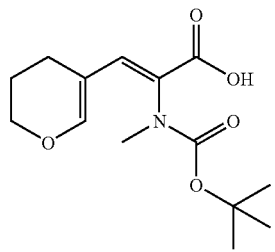

to form a dihydropyran-amine having the formula:

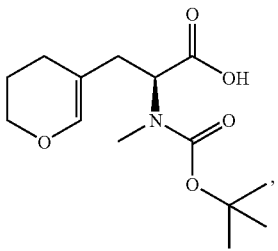

and b) hydrogenating the dihydropyran-amine to form the tetrahydropyran-amine acid.

* * * * *

UNITED STATES PATENT AND TRADEMARK OFFICE
CERTIFICATE OF CORRECTION

PATENT NO. : 8,242,290 B2
APPLICATION NO. : 12/678003
DATED : August 14, 2012
INVENTOR(S) : Paul G. Spoors, Lara S. Kallander and David A. Claremon Page 1 of 1

It is certified that error appears in the above-identified patent and that said Letters Patent is hereby corrected as shown below:

Please delete the following chemical structure at Claim 7, column 19, line 20:

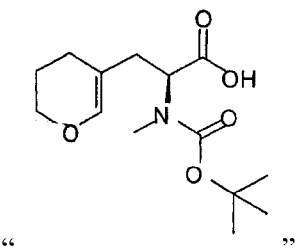

"                "

Please insert the following chemical structure at Claim 7, column 19, line 20 with the following:

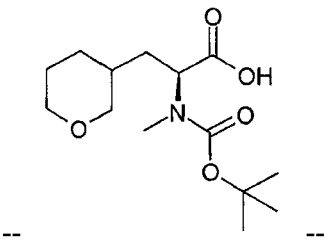

--                    --

Signed and Sealed this
Twenty-third Day of October, 2012

David J. Kappos
*Director of the United States Patent and Trademark Office*